United States Patent
Caro et al.

(10) Patent No.: US 7,982,871 B2
(45) Date of Patent: Jul. 19, 2011

(54) SENSOR FOR IDENTIFYING AT LEAST ONE PARTICLE BY MEANS OF RAMAN-SPECTROSCOPY

(75) Inventors: Jacob Caro, Almere (NL); Jan Mink, Geldrop (NL); Abraham Van Der Gaag, Maarssen (NL)

(73) Assignees: Technische Universiteit Delft, Delft (NL); 2M Engineering Ltd., Veldhoven (NL)

(*) Notice: Subject to any disclaimer, the term of this patent is extended or adjusted under 35 U.S.C. 154(b) by 99 days.

(21) Appl. No.: 12/615,970

(22) Filed: Nov. 10, 2009

(65) Prior Publication Data
US 2010/0141940 A1 Jun. 10, 2010

Related U.S. Application Data

(63) Continuation-in-part of application No. PCT/EP2008/055860, filed on May 13, 2008.

(30) Foreign Application Priority Data

May 11, 2007 (EP) ..................................... 07108065

(51) Int. Cl.
*G01J 3/44* (2006.01)
(52) U.S. Cl. ....................................................... 356/301
(58) Field of Classification Search ................... 356/301
See application file for complete search history.

(56) References Cited

U.S. PATENT DOCUMENTS

| 7,079,240 B2 * | 7/2006 | Scherer et al. ................ 356/318 |
| 2004/0012778 A1 | 1/2004 | Li et al. |
| 2006/0056463 A1 | 3/2006 | Wang et al. |
| 2006/0119853 A1 | 6/2006 | Boumberg et al. |
| 2006/0164635 A1 | 7/2006 | Islam et al. |

FOREIGN PATENT DOCUMENTS

WO WO-2006130728 12/2006

OTHER PUBLICATIONS

Ramser, Kerstin et al., "A Microfluidic System Enabling Raman Measurements of the Oxygenation Cycle in Single Optically Trapped Red Blood Cells", *The Royal Society of Chemistry*, Lab Chip 2005, vol. 5., Feb. 21, 2005, pp. 431-436.

* cited by examiner

*Primary Examiner* — Tari Chowdhury
*Assistant Examiner* — Abdullahi Nur
(74) *Attorney, Agent, or Firm* — Jeffrey D. Myers; Jacques van Breda; Peacock Myers, P.C.

(57) ABSTRACT

A sensor for identifying at least one particle by means of Raman-spectroscopy, comprising an optical trapping system for the at least one particle, including a laser-beam source, acting further as a Raman excitation source for the at least one particle, and a Raman-spectrometer for measuring the spectrally modified light scattered by the at least one particle and for identifying same, wherein the optical trapping system comprises a photonic crystal directly linked with the laser-beam source, which photonic crystal has multiple cavities at predetermined positions, and wherein the laser-beam source in use resonantly excites one or more predetermined electromagnetic modes of the cavities at said positions for trapping and Raman-exciting the at least one particle.

6 Claims, 1 Drawing Sheet

SENSOR FOR IDENTIFYING AT LEAST ONE PARTICLE BY MEANS OF RAMAN-SPECTROSCOPY

This application is a continuation-in-part application of international Patent Application Serial No. PCT/EP2008/055860, entitled "Sensor for Identifying at Least One Particle by Means of Raman-Spectroscopy", to Technische Universiteit Delft, KIWA Water Research B.V. and 2M Engineering Ltd., filed on May 13, 2008, and the specification and claims thereof are incorporated herein by reference.

This application claims priority to and the benefit of the filing of European Patent Application Serial No. 07108065.9, entitled "Sensor for identifying at least one particle by means of raman-spectroscopy", filed on May 11, 2007, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The invention relates to a sensor for identifying at least one particle by means of Raman-spectroscopy, comprising an optical trapping system for the at least one particle, including a laser-beam source, acting further as a Raman excitation source for the at least one particle, and a Raman-spectrometer for measuring the spectrally modified light scattered by the at least one particle and for identifying same.

2. Description of Related Art

The article "Identification of Single Bacterial Cells in Aqueous Solution Using Confocal Laser Tweezers Raman Spectroscopy" by C. Xie et al., published in Analytical Chemistry, 2005, vol. 77, no. 4390-4397 reports on a rapid method for reagentless identification and discrimination of single bacterial cells in aqueous solutions using a combination of laser tweezers and confocal Raman-spectroscopy. The optical trapping enables capturing of individual bacteria in an aqueous solution in the focus of the laser beam, and levitating the captured cell well off a cover plate, thus maximizing the excitation and collection of Raman scattering from the cell and minimizing the unwanted background from the cover plate and environment. Raman spectral patterns excited by a near-infrared laser beam provide intrinsic molecular information for reagentless analysis of the optically isolated bacterium.

Although according to the article a rapid identification of single bacterial cells in an aqueous solution is possible, the sensor set up used therefore was experimental and not suited for wide spread use at distributed places throughout the world at which monitoring for harmful particles is a continuous need. This may relate to outlets for drinking water but also specific applications in a hospital environment or elsewhere.

With the invention it is aimed to provide a sensor which is suitable for such wide spread and local use where no extensive laboratory equipment is available.

A sensor according to the preamble of claim 1 is further known from WO-A-2006/130728.

SUMMARY DESCRIPTION OF THE INVENTION

The sensor of the invention is characterized by one or more of the appended claims.

In a first aspect of the invention the sensor is characterized in that the optical trapping system comprises a photonic crystal directly linked with the laser-beam source, which photonic crystal has multiple cavities at predetermined positions, and wherein the laser-beam source in use resonantly excites one or more predetermined electromagnetic modes of the cavities at said positions for trapping and Raman-exciting the at least one particle, wherein the photonic crystal, the laser beam source and the Raman-spectrometer are housed in a unitary device having an inlet and an outlet for a fluid carrying during operation the at least one particle through the device, wherein a fluid channel connects the inlet to the outlet, and wherein boundary walls of the fluid channel are formed by the Raman spectrometer and the photonic crystal.

In this way the sensor is very suitable for use at a selected site providing as it were a laboratory on a chip, particularly when in the preferred situation the laser-beam source is selected to be at least one semi-conductor laser, and the photonic crystal is made of a material that is compatible with the semi-conductor material of said laser. This facilitates the integration and miniaturization of the sensor of the invention.

DETAILED DESCRIPTION OF THE INVENTION

It is remarked that US-A1-2006/119853 relates to Raman spectroscopy, in particular surface enhanced Raman spectroscopy ("SERS"). This document teaches the use of a thin metal film deposited on a dielectric substrate patterned in the form of a photonic crystal to extract a SERS-signal from low concentrations of analyte molecules embedded inside the photonic crystal lattice, therewith enhancing the Raman-signal.

The beauty of the invention is however that the photonic crystal has cavities that act both as trapping units for the particles to be identified, as well as means for providing Raman-excitation to said particles without the need to apply and excite a metal's surface or a metalloelectric film on a substrate's surface. The energy required herefore stems from the laser-beam source that is directly linked to the photonic crystal and that resonantly excites electromagnetic modes of the cavities of the photonic crystal. Through the use of multiple cavities the chance of any particle getting trapped so as to be able to identify same is virtually 100%.

It is preferred that the walls of the fluid channel are at a distance which is smaller than approximately twice the particles' diameter. A doubled efficiency can be obtained with a design that is based on a photonic crystal membrane that acts as a central wall of a fluidic system, with separate Raman spectrometers for measurement of the emitted spectrum on opposite sides thereof.

It is further preferable that the laser source and/or the photonic crystal is switchable between an on-position and an off-position. When the laser and the photonic crystal are in the on-position, the at least one particle can become trapped and Raman-excited, whereas when the laser source or the photonic crystal is subsequently placed in the off-position the at least one particle is released so as to allow it to continue with the flow of the fluid going through the device. A quasi-continuous operation is then possible as opposed to single-shot operation. Equivalently one could add further optical or electrical means to execute the switching of the light beam to and away from the cavities for trapping and Raman exciting.

The sensor of the invention can advantageously be used with a particle that is selected from the group comprising micro-organisms (bacteria, viruses, fungi and spores), single cell organisms (algae, protozoa) and body fluid cells.

To ease the use of the sensor of the invention it is preferable that the Raman-spectrometer is provided with a memory with data representing typical Raman spectra for preselected particles, and that it includes a discriminator for selecting one of the preselected particles having a Raman spectrum that best matches a current Raman-spectrum measurement.

The discriminator thus provides the answer as to which particle has been sensed and identified.

DESCRIPTION OF THE DRAWING AND THE INVENTION

The invention will hereinafter be further elucidated with reference to the drawing showing in a single FIGURE a schematic set up of a sensor according to the invention.

It will be understood by the person skilled in the art that the following description as well as the previous discussion merely serve to elucidate the appended claims without limiting the claims to anything less than the equitable protection that should follow from the appended claims, and without necessarily limiting same to their literal reading.

DESCRIPTION OF THE DRAWING

The single FIGURE 1 which is attached hereto shows with reference numeral 1 the sensor of the invention for identifying at least one particle by means of Raman-spectroscopy.

DETAILED DESCRIPTION OF THE INVENTION

Figure 1:
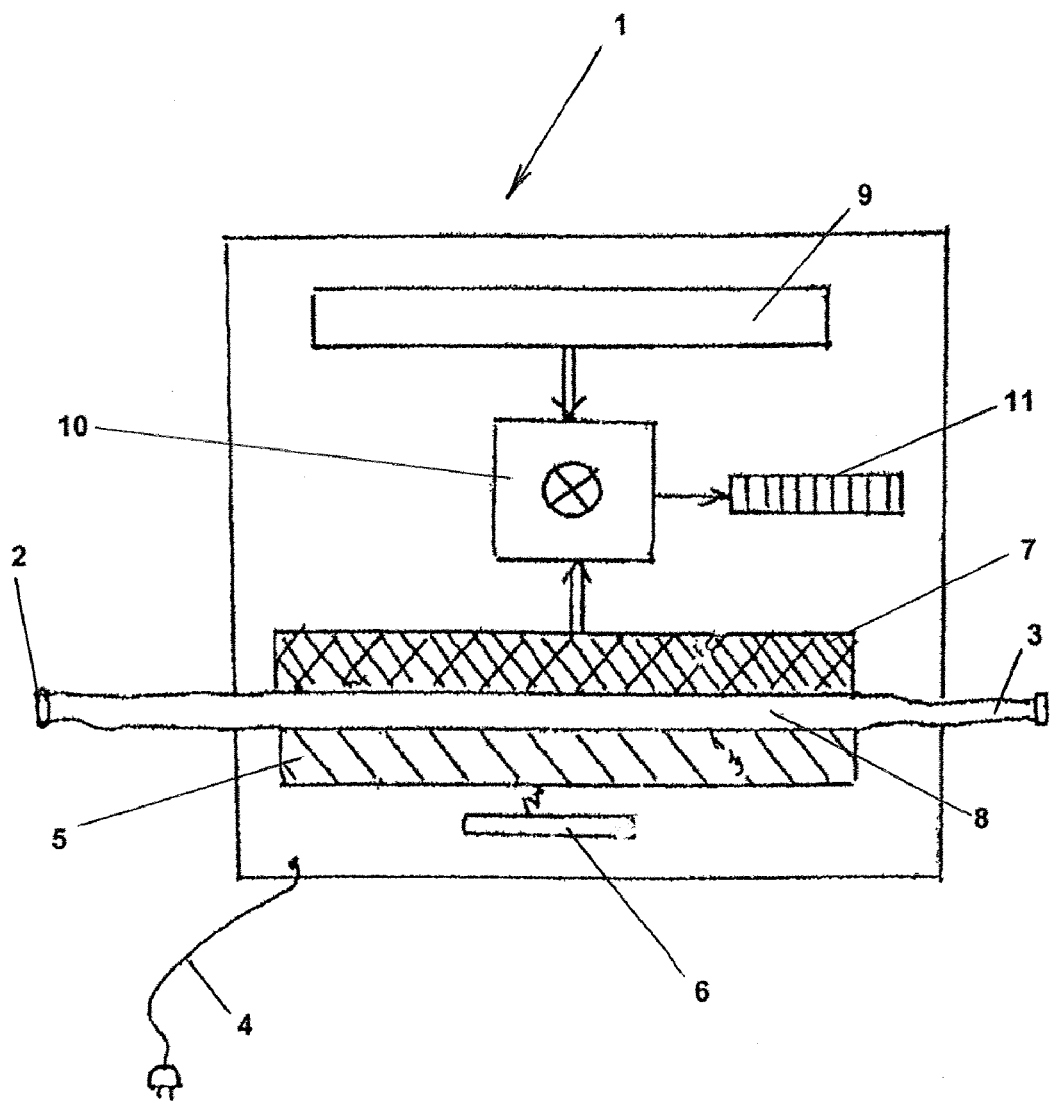

The particles to be investigated flow through the sensor 1 by means of a fluid which enters the sensor 1 at the inlet 2 and exits the sensor 1 at the outlet 3. Between inlet 2 and outlet 3 the Raman-spectroscopy takes place.

In view of the fact that the sensor 1 is a stand-alone device it can operate either by means of a battery or by means of connection to a power outlet to which it may be connected through an electrical cord 4.

The sensor 1 is, as FIGURE 1 shows, a unitary device in which a photonic crystal 5, a laser-beam source 6 and a Raman-spectrometer 7 are housed. As the FIGURE shows the photonic crystal 5 and the Raman-spectrometer 7 are at opposite sides of a fluid channel 8 connecting the inlet 2 with the outlet 3 of the sensor 1. Preferably the Raman spectrometer 7 and the photonic crystal 5 form boundary walls of said fluid channel 8.

When a fluid with the particles to be determined flows through the fluid channel 8 of the sensor 1, the laser-beam source 6 is in an on-position meaning that it is active. The laser-beam source 6 transmits its light signals in the direction of the photonic crystal 5, the cavities of which are due thereto getting into a resonance such that the particles getting in the vicinity of said cavities become optically trapped and also Raman-excited. The Raman scattered light originating from the excited particles is in real-time collected by the Raman-spectrometer 7 and this measured Raman-spectrum is considered to be a fingerprint for the particle that is currently being measured by the sensor 1.

In order to identify the concerning particle, the sensor 1 is provided with a memory 9 that is filled with data representing typical Raman-spectra for pre-selected particles.

Further the sensor 1 comprises a discriminator 10 which carries out a comparison between the actually measured Raman-spectrum by the Raman-spectrometer 7, and the data that is provided in the memory 9. Eventually the discriminator selects one of the pre-selected particles from the memory 9 that has a Raman-spectrum that best matches the currently measured Raman-spectrum by the Raman-spectrometer 7, and displays same in the display 11. The memory 9, discriminator 10 and display 11 can be integrated in a single device. It is noted that also other solutions are possible such as a simple indication whether the measured particle is dangerous or not for peoples' health.

The sensor 1 of the invention is well suited for measuring the suitability for human use of drinking water. The application of the sensor of the invention is however not limited to this application, also other applications in the medical and/or pharmaceutical field are envisaged.

The use of the sensor of the invention over prior art methods provides many advantages.

Prior art methods for sensing of bacteria in water are off line and involve laborious and time consuming methods such as culture growing methods and DNA-amplification techniques or a combination thereof.

By using the sensor of the invention measurements can be performed approximately ten times as fast as in the prior art, and providing many advantages in very diverse applications ranging from online monitoring of industrial processes to establishing at distant sites the suitability of water for human consumption.

What is claimed is:

1. Sensor for identifying at least one particle by means of Raman spectroscopy, comprising an optical trapping system for the at least one particle, including a laser-beam source, acting further as a Raman excitation source for the at least one particle, and a Raman-spectrometer for measuring the spectrally modified light scattered by the at least one particle and for identifying same, wherein the optical trapping system comprises a photonic crystal directly linked with the laser beam source, which photonic crystal has multiple cavities at predetermined positions, and wherein the laser beam source in use resonantly excites one or more predetermined electromagnetic modes of the cavities at said positions for trapping and Raman-exciting the at least one particle, wherein the photonic crystal, the laser-beam source and the Raman-spectrometer are housed in a unitary device having an inlet and an outlet for a fluid carrying during operation the at least one particle through the device, wherein a fluid-channel connects the inlet and the outlet, and wherein said fluid channel has boundary walls formed by the Raman-spectrometer and the photonic crystal.

2. Sensor according to claim 1, wherein the walls of the fluid channel are at a distance which is smaller than approximately twice the particle's diameter.

3. Sensor according to claim 1, wherein the laser beam source is at least one semiconductor laser, and the photonic crystal is made of material that is compatible with the semiconductor material of said laser.

4. Sensor according to claim 1, wherein the laser source and/or the photonic crystal is switchable between an on-position and an off-position.

5. Sensor according to claim 1, wherein the at least one particle is selected from the group comprising micro-organisms, single cell organisms, body fluid cells.

6. Sensor according to claim 1, wherein the Raman-spectrometer is provided with a memory with data representing typical Raman spectra for preselected particles, and that it includes a discriminator for selecting one of the preselected particles having a Raman spectrum that best matches a current Raman spectrum measurement.

* * * * *